(12) United States Patent
Troxell et al.

(10) Patent No.: US 12,102,763 B2
(45) Date of Patent: Oct. 1, 2024

(54) OXYGEN PEP CANNULA

(71) Applicant: KONINKLIJKE PHILIPS N.V., Eindhoven (NL)

(72) Inventors: David Aaron Troxell, San Luis Obispo, CA (US); William Truschel, Oakmont, PA (US); Raymond Hoffman, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 814 days.

(21) Appl. No.: 17/317,077

(22) Filed: May 11, 2021

(65) Prior Publication Data
US 2021/0370004 A1 Dec. 2, 2021

Related U.S. Application Data

(60) Provisional application No. 63/031,633, filed on May 29, 2020.

(51) Int. Cl.
*A61M 16/06* (2006.01)
*A61M 16/08* (2006.01)
*A61M 16/20* (2006.01)

(52) U.S. Cl.
CPC .... *A61M 16/0672* (2014.02); *A61M 16/0816* (2013.01); *A61M 16/208* (2013.01)

(58) Field of Classification Search
CPC .......... A61M 16/0666; A61M 16/0672; A61M 16/208; A61F 5/56; A62B 23/06
See application file for complete search history.

(56) References Cited

U.S. PATENT DOCUMENTS

| | | | |
|---|---|---|---|
| 5,113,857 A | 5/1992 | Dickerman | |
| 5,385,140 A * | 1/1995 | Smith | A61M 15/0018 128/203.29 |
| 10,314,999 B1 | 6/2019 | Lei | |
| 2003/0116163 A1 | 6/2003 | Wood | |
| 2007/0277832 A1* | 12/2007 | Doshi | A62B 23/06 128/207.18 |
| 2007/0295338 A1* | 12/2007 | Loomas | A61M 15/08 128/207.18 |

(Continued)

FOREIGN PATENT DOCUMENTS

KR 200149401 Y1 * 6/1999
KR 101505648 B1 * 3/2015

(Continued)

OTHER PUBLICATIONS

International Search Report for PCT/EP2021/063251 filed May 19, 2021.

(Continued)

*Primary Examiner* — Kathryn E Ditmer
(74) *Attorney, Agent, or Firm* — Daniel H. Brean

(57) ABSTRACT

A cannula configured to provide positive expiratory pressure (PEP) and oxygen to a patient, including: a base including an oxygen opening and an inhalation opening; a valve including an inhalation flap valve that closes the inhalation opening and a PEP flap valve; a valve retainer including a flow opening and an exhalation opening, wherein the PEP flap valve closes the exhalation opening; and a nasal pillow seated on the valve retainer.

19 Claims, 10 Drawing Sheets

(56) References Cited

U.S. PATENT DOCUMENTS

| | | | |
|---|---|---|---|
| 2009/0145441 A1* | 6/2009 | Doshi | A61M 15/085 128/207.18 |
| 2009/0187113 A1* | 7/2009 | Friedman | A61M 16/085 600/543 |
| 2009/0194100 A1* | 8/2009 | Minagi | A61F 5/08 128/200.24 |
| 2011/0284001 A1 | 11/2011 | Tero | |
| 2012/0085347 A1 | 4/2012 | Colbaugh | |
| 2013/0000647 A1* | 1/2013 | Holley | A61F 5/566 128/207.13 |
| 2013/0081637 A1* | 4/2013 | Foley | A61F 5/08 128/848 |
| 2014/0366880 A1 | 12/2014 | Metz | |
| 2015/0040907 A1* | 2/2015 | Hakim | A63B 23/18 128/205.24 |
| 2015/0209541 A1 | 7/2015 | Harwood | |
| 2015/0250973 A1* | 9/2015 | Allum | A61M 16/201 128/205.25 |
| 2016/0030229 A1* | 2/2016 | Goldschmidt | A61M 16/201 128/847 |
| 2016/0082209 A1* | 3/2016 | Witt | A61M 16/0057 128/204.23 |
| 2017/0007794 A1* | 1/2017 | Atherton | A61M 16/125 |
| 2017/0304575 A1 | 10/2017 | Boulanger | |
| 2017/0368278 A9 | 12/2017 | Costella | |
| 2018/0326173 A1* | 11/2018 | Ewers | A61M 16/0666 |
| 2019/0001187 A1 | 1/2019 | Collins | |
| 2019/0030274 A1* | 1/2019 | Rashidi | A61M 16/0666 |
| 2019/0366018 A1* | 12/2019 | Conlon | A61M 15/0021 |
| 2020/0155783 A1 | 5/2020 | Allum | |
| 2021/0137723 A1* | 5/2021 | Kanwar | A61F 5/56 |
| 2022/0008685 A1* | 1/2022 | Igarashi | A61M 16/0866 |

FOREIGN PATENT DOCUMENTS

| | | |
|---|---|---|
| KR | 102044469 B1 * | 11/2019 |
| WO | 2009117400 A2 | 9/2009 |
| WO | 2010076704 A1 | 7/2010 |
| WO | 2018109006 A1 | 6/2018 |

OTHER PUBLICATIONS

Nicolini, A. et al., "Use of positive expiratory pressure during six minute walk test: results in patients with moderate to severe chronic obstructive pulmonary disease". Multidisciplinary Respiratory Medicine 2013, 8:19.

Wibmer, T. et al., "Effects of nasal positive expiratory pressure on dynamic hyperinflation and 6-minute walk test in patients with COPD". Respiratory Care • May 2014 • vol. 59 • No. 5.

Stoller, J.K et al., "Oxygen therapy for patients with COPD, current evidence and the long-term oxygen treatment trial". Chest • 138 • 1 • Jul. 2010.

* cited by examiner

OXYGEN PEP CANNULA

CROSS-REFERENCE TO RELATED APPLICATIONS

This patent application claims the priority benefit under 35 U.S.C. § 119(e) of U.S. Provisional Application No. 63/031,633, filed on May 29, 2020, the contents of which are herein incorporated by reference.

TECHNICAL FIELD

Various exemplary embodiments disclosed herein relate generally to a cannula device that provides both oxygen and positive expiratory pressure (PEP) to a patient using the cannula device.

BACKGROUND

Chronic obstructive pulmonary disease (COPD) is associated with progressive, irreversible worsening of airflow limitation caused by alveolar wall destruction, bronchiolar narrowing, and airway inflammation. Individuals with COPD typically demonstrate a limited capacity to exercise. These individuals typically experience dyspnea during exercise often causing the individual to discontinue the exercise. At rest, COPD patients can often maintain inspiratory capacity (IC) and stable end expiratory lung volume (EELV). During exercise however there is an increased ventilatory (or respiratory) demand, which can exacerbate expiratory flow limitation, increase dynamic hyperinflation, and lead to a rapid-shallow breathing pattern.

Use of positive expiratory pressure (PEP) has been clinically validated to improve functional exercise capacity in individuals with COPD.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a cannula configured to provide positive expiratory pressure (PEP) and oxygen to a patient, including: a base including an oxygen opening and an inhalation opening, a valve including an inhalation flap valve that closes the inhalation opening and a PEP flap valve; a valve retainer including a flow opening and an exhalation opening, wherein the PEP flap valve closes the exhalation opening, and a nasal pillow seated on the valve retainer.

Various embodiments are described, further comprising a nozzle including a plurality of nozzle openings in the oxygen opening of the base.

Various embodiments are described, wherein the nozzle is configured to produce a venturi effect.

Various embodiments are described, wherein the valve retainer further includes a flow opening wall, wherein an edge of the flow opening wall is an inhalation flap valve stop.

Various embodiments are described, wherein the valve retainer includes a leg with a leg notch at the end of the leg, and the base includes a tab configured to engage the leg notch.

Various embodiments are described, wherein the PEP flap valve provides a static PEP value.

Various embodiments are described, wherein PEP flap valve includes a biasing member configured to provide a static PEP value.

Various embodiments are described, further including a plug configured to be placed in the oxygen opening.

Various embodiments are described, wherein the valve retainer includes an outer wall and wherein a portion of the outer wall adjacent to the exhalation opening is a PEP flap seal.

Various embodiments are described, wherein the base further includes an oxygen opening wall, wherein an edge of the oxygen opening wall is an inhalation flap seal.

Various embodiments are described, wherein the inhalation flap valve is configured to open the inhalation opening when the patient inhales.

Various embodiments are described, wherein the PEP flap valve is configured to open the exhalation opening when the patient exhales and to provide a static PEP value.

Further various embodiments relate to a cannula device configured to provide positive expiratory pressure (PEP) and oxygen to a patient, including: two cannulas wherein the cannulas comprise: a base including an oxygen opening and an inhalation opening, a first valve including an inhalation flap valve that closes the inhalation opening and a PEP flap valve; a valve retainer including a flow opening and an exhalation opening, wherein the PEP flap valve closes the exhalation opening, and a nasal pillow seated on the valve retainer; a connector connecting the two cannulas to one another; and an oxygen hose configured to connect to the base.

Various embodiments are described, further including a second valve, wherein the first and second valves have different PEP values and wherein the cannulas are configured to exchange the first and second valves.

Various embodiments are described, further including two plugs configured to be placed in the oxygen openings of the two cannulas.

Various embodiments are described, wherein the inhalation flap valve is configured to open the inhalation opening when the patient inhales.

Various embodiments are described, wherein the PEP flap valve is configured to open the exhalation opening when the patient exhales and to provide a static PEP value.

Various embodiments are described, wherein the two cannulas further comprising a nozzle including a plurality of nozzle openings in the oxygen opening of the base.

Various embodiments are described, wherein the nozzle is configured to produce a venturi effect.

Further various embodiments relate to a cannula configured to provide positive expiratory pressure (PEP) and oxygen to a patient, including: a nostril-sealing nasal interface having a body including an inhalation opening and an exhalation opening, an inhalation valve configured to open and close the inhalation opening, the inhalation valve being biased in the closed position; and a PEP valve configured to open and close the exhalation opening, the PEP valve being biased in the closed position, wherein nasal inhalation by a patient causes the inhalation valve to open and the exhalation valve to remain closed, and wherein nasal exhalation by a patient causes the inhalation valve to close and the PEP valve to open, providing a positive expiratory pressure.

Various embodiments are described, further including an oxygen hose configured to connect to the inhalation opening including a venturi valve and an air entrainment opening.

Various embodiments are described, further including an oxygen hose configured to connect to the inhalation opening and an ambient air valve configured to open when the patient inhales and to close when the patient exhales.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
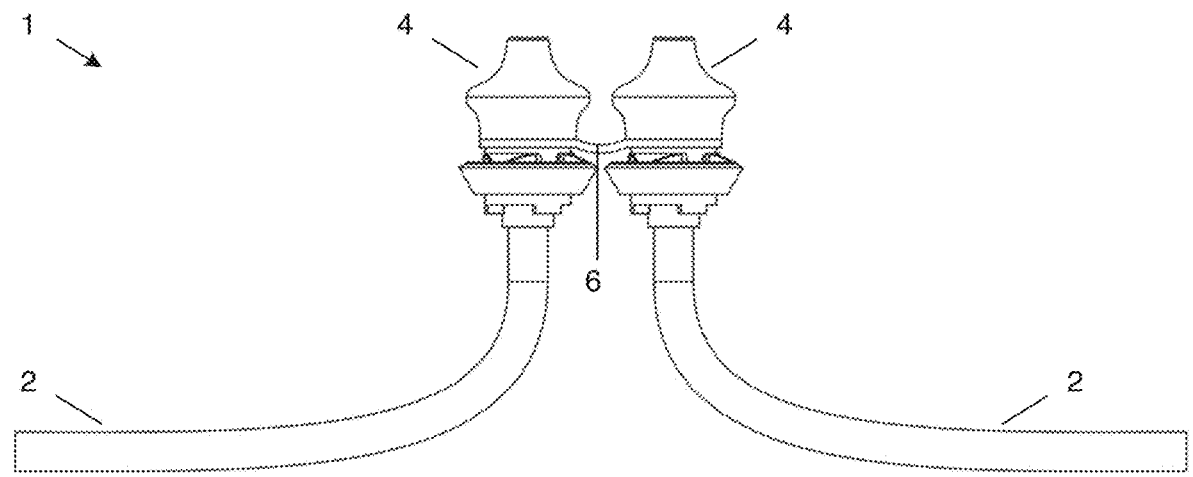
FIG. 1 illustrates an embodiment of the PEP cannula device.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Chronic obstructive pulmonary disease (COPD) is associated with progressive, irreversible worsening of airflow limitation caused by alveolar wall destruction, bronchiolar narrowing, and airway inflammation. Individuals with COPD typically demonstrate a limited capacity to exercise. These individuals typically experience dyspnea during exercise often causing the individual to discontinue the exercise. At rest, COPD patients can often maintain inspiratory capacity (IC) and stable end expiratory lung volume (EELV). During exercise however there is an increased ventilatory (or respiratory) demand, which can exacerbate expiratory flow limitation, increase dynamic hyperinflation, and lead to a rapid-shallow breathing pattern.

Use of positive expiratory pressure (PEP) has been clinically validated to improve functional exercise capacity in individuals with COPD. In addition, the use of PEP overcomes the patients perception of having a shortness of breath. The study referenced utilized a PEP valve with corrugated tubing and a mouthpiece. Exercise capacity between control and therapeutic groups was evaluated using a six minute walk test (6MWT).

A more recent trend has seen the introduction of the HFNC (High Flow Nasal Cannula) therapy in both the acute and homecare space. The various HFNC options available in the market require a 50 PSI gas source or a compressor to operate, are capable of delivering very high liter flows to support ventilation (<70 lpm), are geared for acute care and or homecare use, and often incorporate a venturi valve to increase both entrained air as well as net gas flow rates.

Current systems for providing PEP therapy to patients are bulky or are for example handheld. This makes their use inconvenient or not possible during exercise or even when a patient is carrying on normal daily activities. Embodiments of a PEP cannula device that delivers oxygen as well as PEP therapy will be described herein.

The PEP cannula device described herein offers significant advantages over the prior PEP delivery models as well as the potential of adding PEP to newer more sophisticated HFNC options for oxygen dependent, non-ventilator dependent COPD patients. The potential advantages include the following.

The PEP cannula device provides an adjustable and static PEP values. The first study referenced above utilized a fixed, flow-independent 5 cmH2O PEP valve applied via a mouthpiece which did improve exercise tolerance. The second study utilized a flow resistor applied to an oral-nasal mask which created a flow-dependent variable PEP value estimated between 10-20 cmH2O. The advantage to the first study was clearly the improvement in exercise tolerance as well as a noted improvement in $SpO_2$ and heart rate. The improvement in the second study was the significant improvement in dynamic hyperinflation, however at the cost of decrease in exercise tolerance, decrease $SpO_2$, and increased heart rate.

The PEP cannula device allows for an adjustable or titratable static PEP value that may be individualized and adjusted using evaluation metrics such as the 6MWT, Borg dyspnea scale, $SpO_2$, and heart rate to maximize therapeutic impact on the user. PEP adjustment may be implemented by the user swapping our different parts of the PEP cannula to achieve the desired result.

The cannula incorporates PEP into an oxygen delivery system. The PEP cannula device would offer the previously described advantages of PEP along with the ability to deliver low flow, high flow, or pulse dose oxygen therapy. Long term oxygen therapy (LTOT) has been clinically proven to improve long term survivability in COPD and is thought to improve exercise tolerance. The combination of oxygen therapy and PEP with the PEP cannula invention is believed to hold the potential to further improve the impact on exercise tolerance and dyspnea over one therapy alone.

The PEP cannula device provides on demand PEP engagement. PEP engagement may be controlled by the user, in that oxygen may be engaged by simple, nasal inspiration, whereas PEP engagement can be engaged by nasal expiration, and finally no PEP delivery can be facilitated by oral as opposed to nasal expiration.

The PEP cannula device facilitates user comfort and the ability to wear during ambulation, exercise, and activities of daily living. The lightweight, minimal contact nature of the PEP cannula device improves patient comfort and facilitates expanded use of activities of daily living without significant coordination and technique requirements while being very discreet by design. By comparison if using the current PEP devices, an oxygen-dependent individual with COPD would conceivably need to stop exercise/current activity, retrieve the PEP device, hold the PEP device while focusing on proper technique (e.g., nasal inspiration followed by oral expiration), potentially restricting use of both arms if the other is actively being used to hold on to the oxygen delivery device such as a portable oxygen concentrator.

FIG. 1 illustrates an embodiment of the PEP cannula device 1. The PEP cannula device 1 includes two cannulas 4, a connector 6, and two oxygen supply hoses 2. The connector 6 attaches the two cannulas 4 together so that each cannula may engage the patients nostrils. The oxygen supply hoses 2 are each connected to the cannulas 4 to provide a supply of oxygen for oxygen therapy from an oxygen supply. The oxygen supply may be a portable supply such as for example a portable oxygen cannister or a portable oxygen concentrator. In other embodiments, the oxygen supply may be more fixed supply such as larger oxygen cylinders, oxygen concentrators, or a wall oxygen supply like those found in a hospital. In other embodiments a single oxygen hose may be used that has two outlets that connect to the two cannulas 4. Further, the oxygen hoses 2 may provide the needed structure for the PEP cannula device 1 to be held in place on the patient when worn by the patient. Alternatively, additional headgear may be used to keep the PEP cannula device in place during use.

Figure 2:
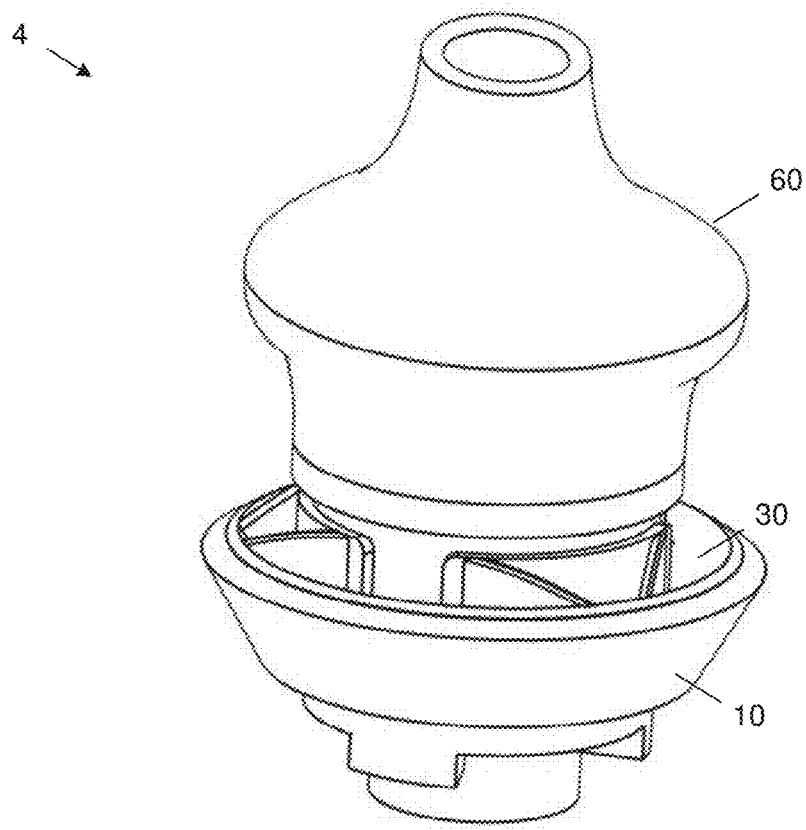
FIG. 2 illustrates a perspective view of the cannula.
Figure 3:
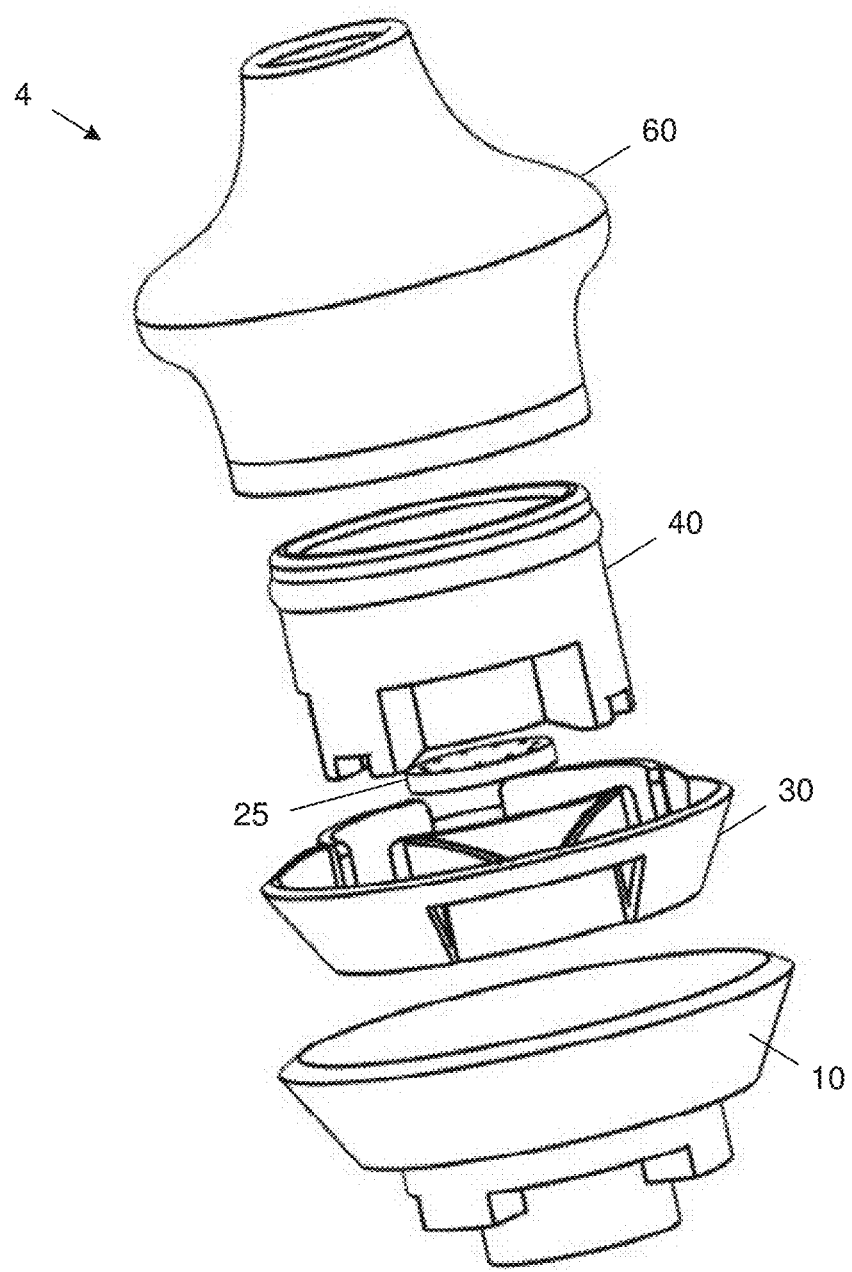
FIG. 3 illustrates an expanded perspective view of the cannula.

FIG. 2 illustrates a perspective view of the cannula 4. FIG. 3 illustrates an expanded perspective view of the cannula 4. The cannula includes a base 10, a valve 30, a nozzle 25, a valve retainer 40, and a nasal pillow 60.

Figure 4:
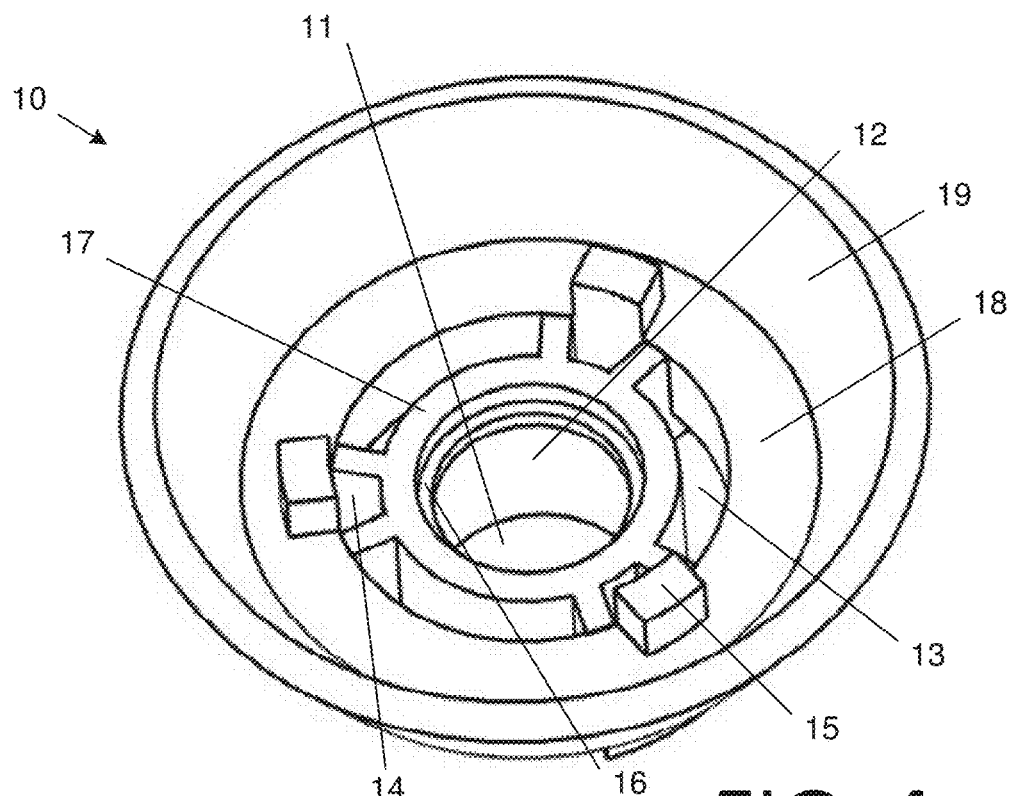
FIGS. 4 and 5 illustrate top and bottom perspective views of the base respectively.
Figure 5:
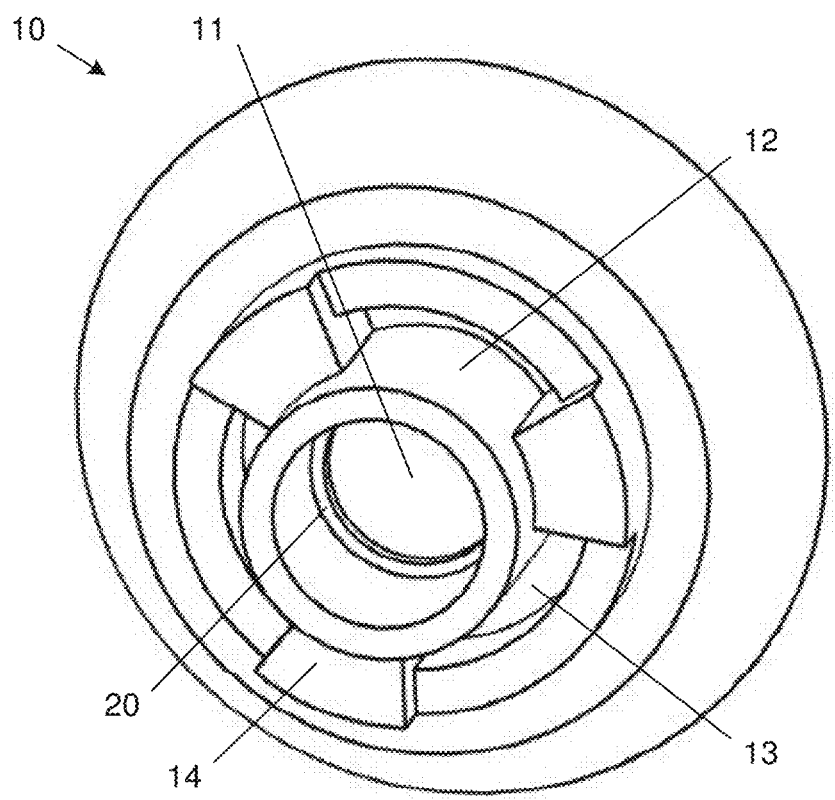

FIGS. 4 and 5 illustrate top and bottom perspective views of the base 10 respectively. The base 10 is located at the bottom of the cannula 4 and provides the connection to the oxygen hose 2. The base 10 includes an oxygen opening 11 formed by an oxygen opening wall 12 that receives the end of the oxygen hose 2. The oxygen opening 11 includes an oxygen hose stop 20. The oxygen hose 2 is inserted into the oxygen opening 11 until it reaches the oxygen hose stop 20. The oxygen opening 11 is surrounded by the oxygen opening wall 12 which engages the oxygen hose 2 and fixes the oxygen hose to the base 10 and hence to the cannula 4. The body 10 also includes a substantially circular annular lower inner surface 18 and a substantially frustoconical body side inner surface 19 that both support valve 30. The body 10 also includes three inhalation openings 13 that are between the oxygen opening wall 12 and the body lower inner surface 18. The inhalation openings 13 will provide the path for ambient air to be inhaled by the patient. The base 10 also includes three inhalation opening separators 14 that help form and separate the inhalation openings 13.

The oxygen opening 11 also includes a nozzle support 16 that supports the nozzle 25 when it is place on the body 10. As shown the nozzle support 16 and the oxygen hose stop 20 are part of the same structure, but in other embodiments they may be separate structures inside the oxygen opening 11. The oxygen opening wall 12 has a top surface that is an inhalation flap seal 17. The inhalation flap seal 17 contacts an inhalation flap valve 31 on the valve 30 (see FIGS. 6 and 7) to inhibit the flow of air through the inhalation opening 13. The body 10 includes three tabs 15 that are located on the body lower inner surface 18 and that are adjacent the inhalation opening separators 14. These tabs 14 will interface with a leg notch 44 on the valve retainer (see FIGS. 9 and 10).

Figure 6:
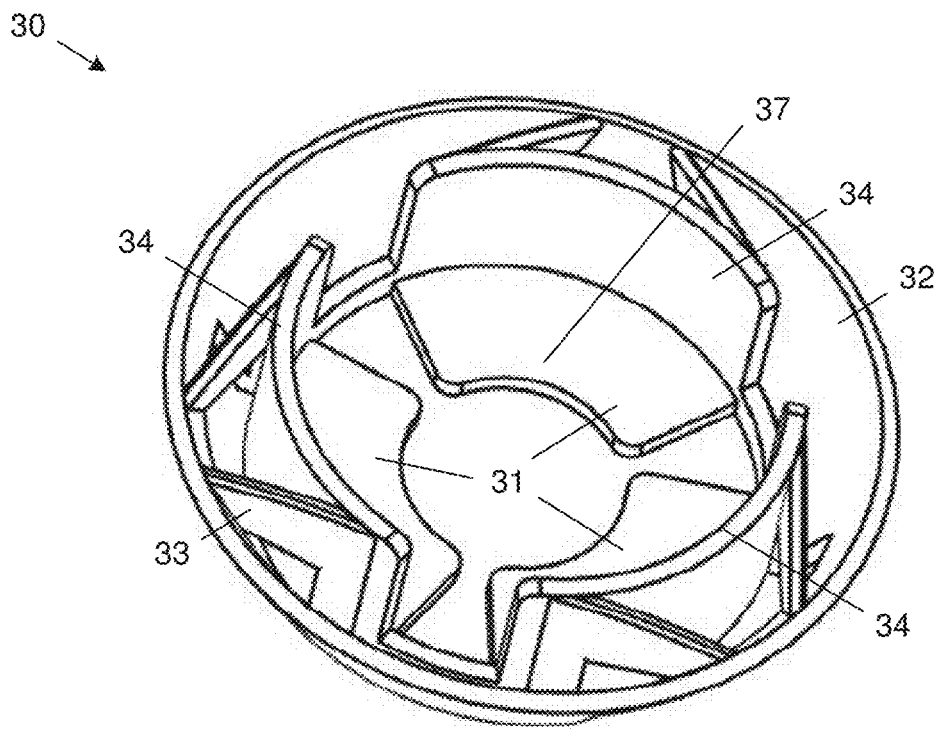
FIGS. 6 and 7 illustrate top and bottom perspective views of the valve respectively.
Figure 7:
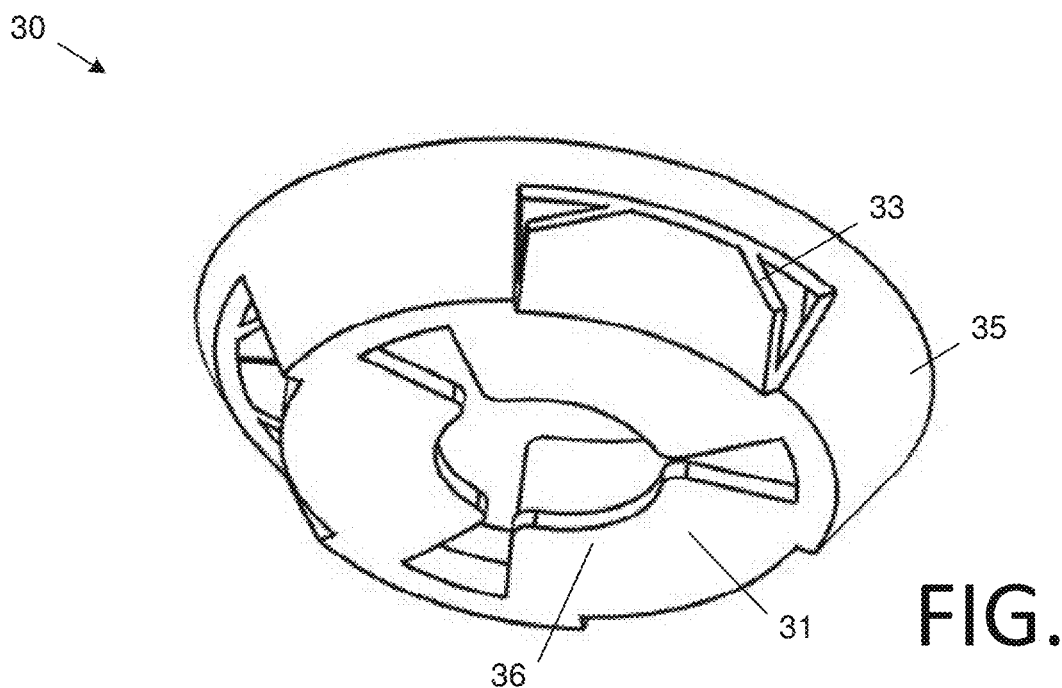

FIGS. 6 and 7 illustrate top and bottom perspective views of the valve respectively. The valve 30 has an outer wall 35 having a substantially frustoconical shape. The valve 30 includes three inhalation flap valves 31 that extend from the valve outer wall 35 towards the center of the valve 30. A portion 36 of the bottom surface of the inhalation flap valve 31 contacts the inhalation flap seal of the body 10. A portion 37 of the top surface of the inhalation flap valve 31 contacts a flap stop 47 on the valve retainer 40 (see FIGS. 9 and 10).

The valve 30 also include three PEP flap valves 34. The PEP flap valves 34 extend in a vertical direction from the inhalation flap valves 31. The valve 30 includes biasing members 33 that provide a flexible connection between the valve inner surface 32 and the PEP flap valves 34. While two biasing members 33 are shown attached to each PEP flap valve 34, more or less biasing members may be used. Further, while the biasing members 33 are shown with a specific shape, other shapes are possible that provide the needed flexible connection between the valve inner surface 32 and the PEP flap valves 34. Further, the biasing members 33 may also be connected at different locations on the valve inner surface 32 and the PEP flap valves 34 than those specifically shown in FIGS. 6 and 7.

The ends of the inhalation flap valves 31 substantially form a circular opening that corresponds to the oxygen opening 11 of the body 10.

The valve 30 may be made an elastomeric material, for example, silicone or thermoplastic elastomer.

Figure 8:
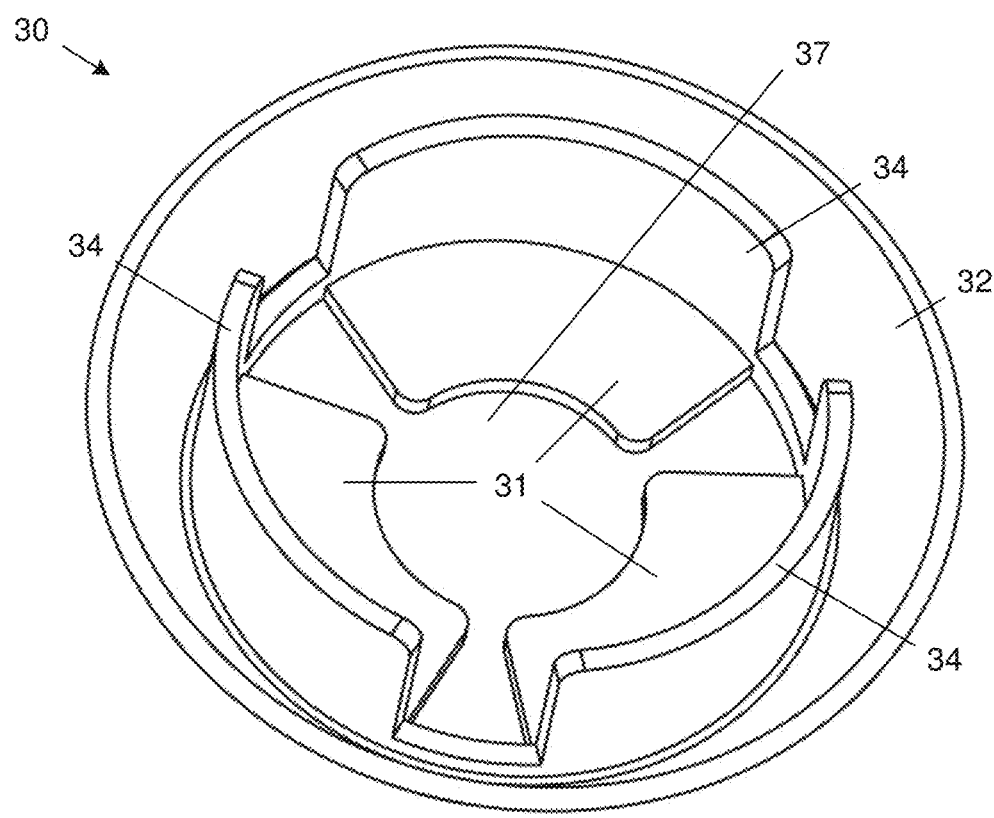
FIG. 8 illustrates another embodiment of the valve.

FIG. 8 illustrates another embodiment of the valve 30. In this embodiment there are no biasing members 33. Instead, the rigidity of the PEP flap valves 34 along with various material dimensions and characteristics of the valve 30 result in a desired PEP value. This may allow for a static PEP value that is based upon the specific characteristics of the PEP flap valves 34 and the valve 30 and is independent of the exhalation pressure or velocity.

Figure 9:
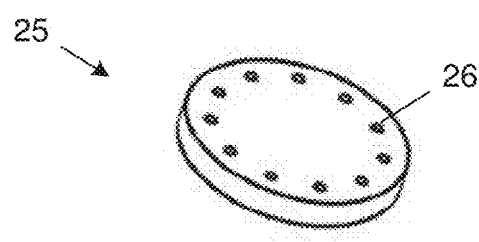
FIG. 9 illustrates a nozzle.

FIG. 9 illustrates a nozzle 25. The nozzle 25 has a plurality of nozzle openings 26. The nozzle 25 fits inside the upper end of the oxygen opening 11 and rests on the nozzle support 16.

Figure 10:
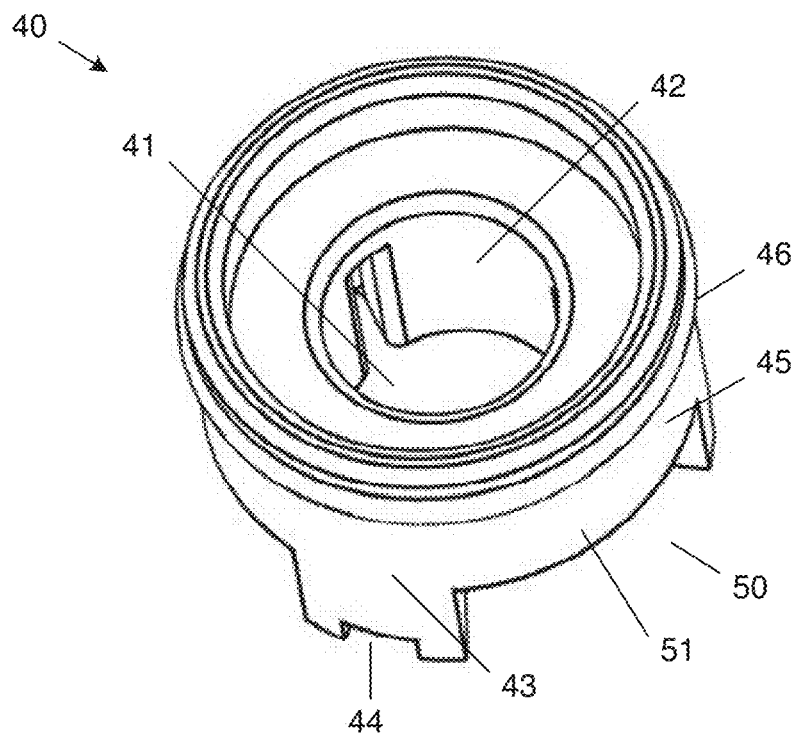
FIGS. 10 and 11 illustrate top and bottom perspective views of the valve retainer respectively.
Figure 11:
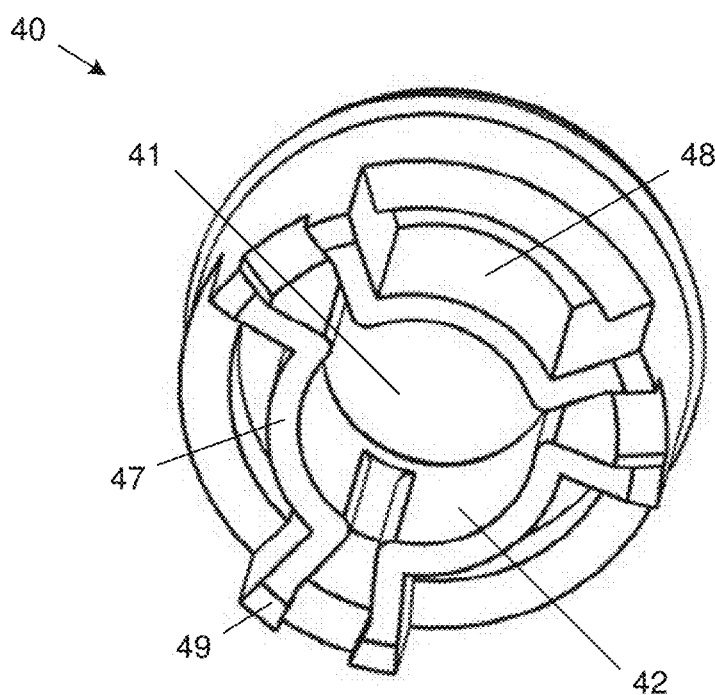

FIGS. 10 and 101 illustrate top and bottom perspective views of the valve retainer, respectively. The valve retainer 40 sits on top of the valve 30 and the base 10 in the cannula 4. The valve retainer 40 includes flow opening 41 that generally aligns with the oxygen opening 11 of the base 10. The flow opening 41 is defined by the flow opening inner wall 42. The wall forming the flow opening 41 also has a flow opening outer wall 48. The valve retainer 40 includes an valve retainer outer wall 45, and extending from the valve retainer outer wall 46 is a nasal pillow ridge. The nasal pillow ridge 46 extends around the valve retainer 40 and is positioned near the top of the valve retainer 40. The nasal pillow ridge 46 engages a nasal pillow retainer 63 of the nasal pillow 60 (see FIG. 13) to secure the nasal pillow to the valve retainer 40.

The valve retainer 40 includes three legs 43 that extend downward, and the legs 43 include a leg notch 44. When the cannula 4 is in its assembled form, the leg notch 44 engages the tabs 15 of the body 10. The legs 43 have a bottom 49 that extends towards the valve 30, and may leave a gap between the bottom 39 and the valve 30. In other embodiments, the bottom 49 may contact the valve 30.

The valve retainer 40 includes a exhalation opening 50 that facilitates air flow out of the cannula 4 when the patient exhales using the PEP cannula device 1. The exhalation opening 50 is between adjacent legs 43, and its operation will be further explained below. The valve retainer 40 includes a PEP flap seal 51 that is a portion of the outer wall 45 that is adjacent the exhalation opening 50. The PEP flap seal 51 contacts an PEP flap valve 34 on the valve 30 to inhibit the flow of air through the exhalation opening 50.

Figure 12:
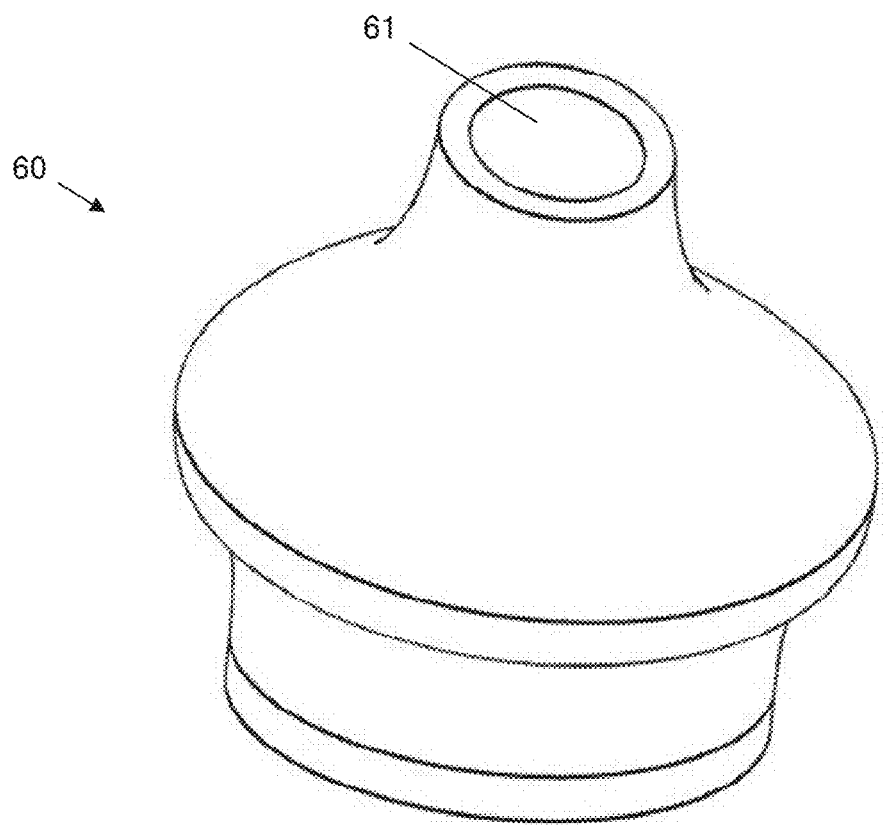
FIGS. 12 and 13 illustrate top and bottom perspective views of the nasal pillow respectively.
Figure 13:
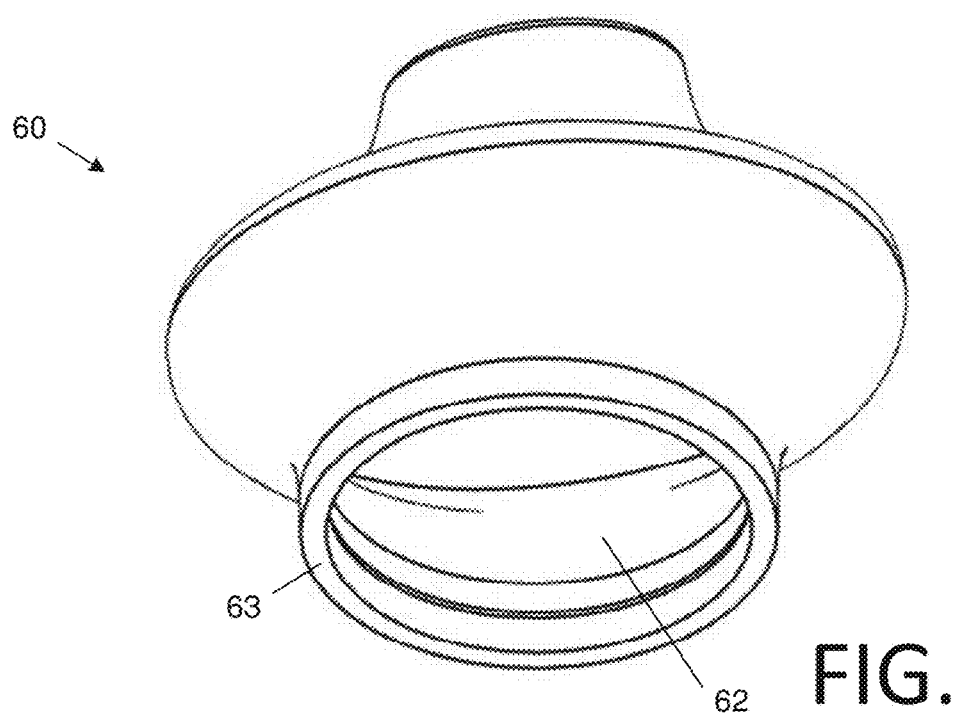

FIGS. 12 and 13 illustrate top and bottom perspective views of the nasal pillow, respectively. The nasal pillow 60 provides a sealed interface between the cannula 4 and the nostrils of a patient. The nasal pillow 60 includes a nasal opening 61 through which air flows between the patients nares and the cannula 4. The nasal pillow also includes a valve retainer opening 62 that interfaces with the valve retainer 40 and is placed over the valve retainer 40. A nasal pillow retainer 63 interfaces with the nasal pillow ridge 46 to secure the nasal pillow 60 to the valve retainer 40 and also to provide an airtight connection between the nasal pillow 60 and the valve retainer 40. The nasal pillow 60 will be made of a material that is flexible and comfortable to the patient. It will also be made from a material that facilitates an airtight or substantially airtight interface between the patient's nose and the nasal pillow 60. The nasal pillow may be made an elastomeric material, for example, silicone or thermoplastic elastomer.

Figure 14:
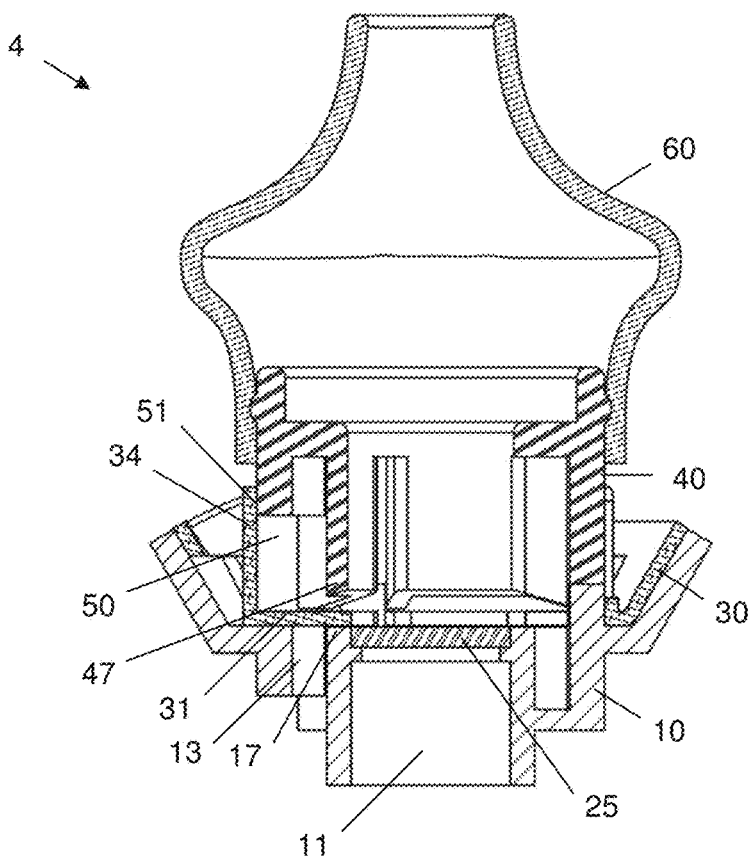
FIG. 14 illustrates a cross-sectional view of the cannula.
Figure 15:
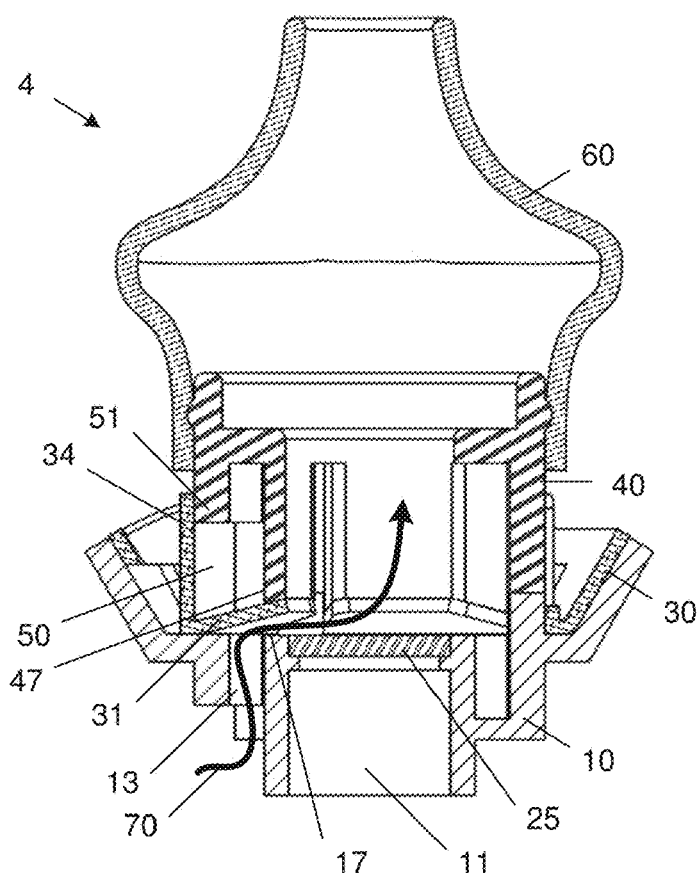
FIG. 15 illustrates the operation of the cannula when the patient inhales.
Figure 16:
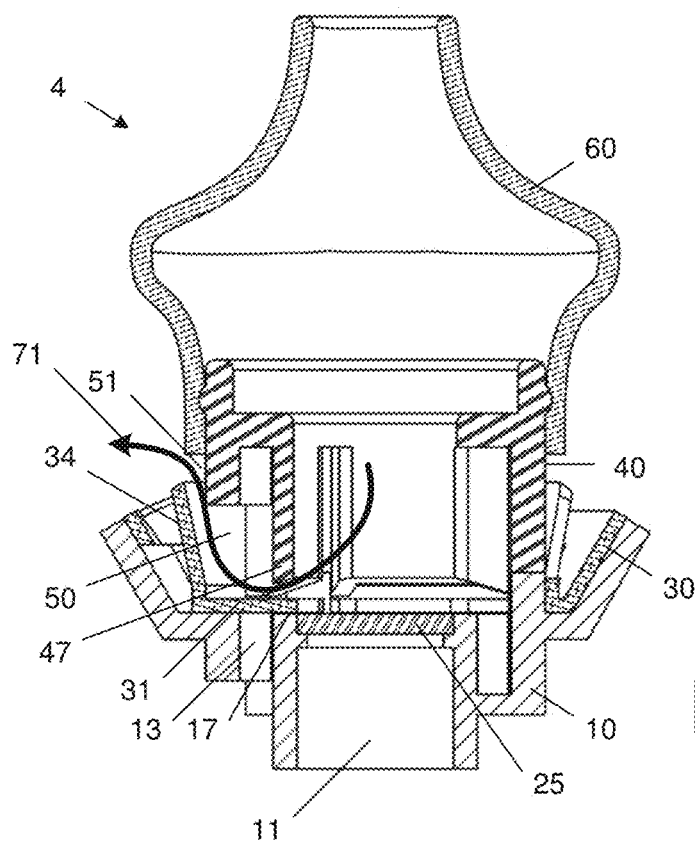
FIG. 16 illustrates the operation of the cannula when the patient exhales.

FIG. 14 illustrates a cross-sectional view of the cannula 4. FIGS. 14-16 will be used to explain the operation of the cannula 4. In FIG. 14, the cannula is shown in a state where there is no inhalation or exhalation. Oxygen from the oxygen hose 2 (not shown) flows into the oxygen opening 11. The oxygen then flows through the nozzle openings 26 in the nozzle 25 into the valve retainer 40 and then the nasal pillow 60. The nozzle openings 26 can lead to a venturi effect when the patient inhales. In FIG. 14 the inhalation flap valve 31 is in contact with inhalation flap seal 17 that prevents any air flow through the inhalation opening 13. Further, the PEP flap valve 34 is in contact with the PEP flap seal 51 that prevents any air flow through the exhalation opening 50.

FIG. 15 illustrates the operation of the cannula 4 when the patient inhales. When the patient inhales this creates a negative air pressure on the top side of the inhalation flap valve 31 that causes the inhalation flap valve 31 to rise until it contacts the flap stop 47. This then allows ambient air to be drawn in along the inhalation air path 70. This ambient air is then mixed in the valve retainer and nasal pillow with the inflow of oxygen from the oxygen hose. If the nozzle openings 26 create a venturi effect, then this entrains the ambient air to assist in the inhalation air flow as well as additional negative pressure to assist in opening the inhalation flap valve 31. Once the patient ceases inhaling, the inhalation flap valve 31 will return back into contact with the inhalation flap seal 17 to stop the flow of ambient air. This may be accomplished because the material of the inhalation flap valve 31 will seek to return to its original shape. It is noted that as the patient inhales the negative pressure created causes the PEP flap valve 34 to stay firmly closed and in contact with the PEP flap seal 51 that prevents any air flow through the exhalation opening 50.

FIG. 16 illustrates the operation of the cannula 4 when the patient exhales. When the patient exhales this creates a positive air pressure on the inside of the PEP flap valve 34 that causes the PEP flap valve 31 to move away from the PEP flap seal 51 and this results in an opening. This then allows the exhaled air to flow along the exhalation air path 71 out through the exhalation opening 50 and out of the cannula 4. Once the patient ceases exhaling, the PEP flap valve 34 will spring back into contact with the PEP flap seal 51 to stop the flow of air along the exhalation air path 71. It is noted that as the patient exhales the positive pressure created causes the inhalation flap valve 31 to stay firmly closed and in contact with the inhalation flap seal 17 that prevents any air flow through the inhalation opening 13.

The biasing members 33 may be designed with various material dimensions and characteristics to result in different stiffness values for the biasing members 33. The biasing members also allow for a static PEP value that is based upon the specific characteristics of the biasing members 33 and is independent of the exhalation pressure or velocity. Accordingly, the patient may be provided a PEP cannula device 1 with a number of different valves 30 that have different PEP values. The patient may easily exchange the different valves and determine which valve provides the best PEP therapy and benefit. This allows for an adjustable and titratable PEP value for the patient.

During cyclic breathing by the patient through the cannula 4, the inhalation flap valve 31 and the PEP flap valve 34 work in unison together to open and close the inhalation air path 70 and the exhalation air path 71. During inhalation, the inhalation flap valve 31 opens to allow ambient air into the cannula to mix with the oxygen from the oxygen source, and the PEP flap valve 34 is securely pulled closed because of the negative pressure created by the patients inhalation. During exhalation, the PEP flap valve 34 opens to allow the exhaled air to exit the cannula 4 through the exhalation opening 50, and the inhalation flap valve is securely pushed closed because of the positive pressure created by the patient inhalation.

The location of the nozzle 25 in the oxygen opening 11 will determine the venturi affect provided by the incoming oxygen flow. As shown in FIG. 15, the nozzle 25 may be positioned higher or lower in the oxygen opening 11 to determine the specific venturi affect that is provided by the nozzle. Also, the location of the nozzle relative to the location of the inhalation opening 13 will determine the overall venturi affects as well. Accordingly, the nozzle 25 and the inhalation openings 13 will be positioned to obtain the desired venturi affect.

It is also noted that the cannula 4 may not have a nozzle 25, in which case the oxygen flow from the oxygen hose 2 will mix with ambient air that flows in through the inhalation opening 13 when the patient inhales.

In another embodiment, the patient may only need to use the PEP cannula device 1 for PEP therapy without oxygen therapy. This may be implemented by using a plug (not shown) that may be fitted into the oxygen opening 11 to prevent the air exhaled by the patient to flow out through the oxygen opening 11 and allowing it to instead flow along the exhalation path 71 through the PEP flap valve 34 that provides the desired PEP therapy. In another implementation, the inhalation flap valves may extend to cover the oxygen opening 11 to prevent the air exhaled by the patient from flowing out through the oxygen opening 11 and allowing it to instead flow along the exhalation path 71 through the PEP flap valve 34 that provides the desired PEP therapy.

In describing the cannula, three inhalation flap valves 31 and three PEP flap valves 34 were described. This leads to a corresponding number of inhalation openings 13, exhalation openings 50, legs 43, tabs 15 etc. It is noted that the number of inhalation flap valves 31 and PEP flap valves 34 could be fewer or more.

Figure 17:
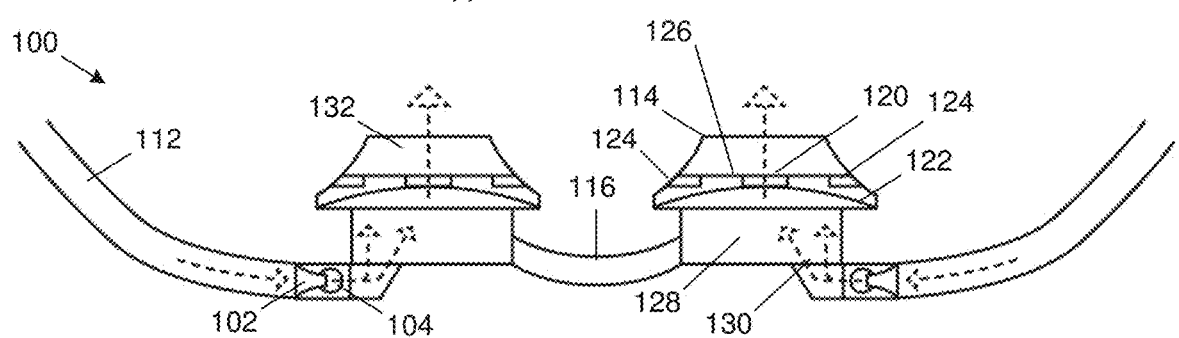
FIGS. 17 and 18 illustrate another embodiment of a PEP cannula device during inhalation and exhalation respectively.
Figure 18:
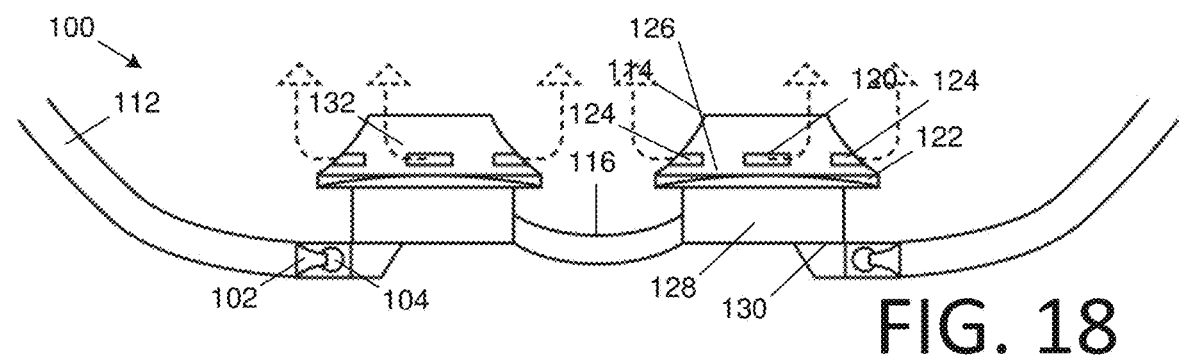

Another embodiment of a PEP cannula device 100 will now be described. FIGS. 17 and 18 illustrate another embodiment of a PEP cannula device 100 during inhalation and exhalation, respectively. The PEP cannula device 100 includes cannulas 114, connector 116, and oxygen hoses 112. The oxygen hoses may further include a venturi valve 102 and entrainment opening 104. The venturi valve 102 creates a venturi affect that entrains ambient air drawn in through the entrainment opening 104 with the oxygen supplied through the oxygen hose 112.

The cannula 114 includes a body 128 with an air opening 130. The oxygen hose 112 is connected to the to the air opening 130 to supply oxygen and ambient air to the cannula 114.

The cannula 114 also includes a nasal interface 132 with exhalation openings 124, an inhalation flap 120, a PEP spring 122, and an exhalation plate 126. The inhalation flap 120 in on an opening in the exhalation plate 126. The PEP spring 122 biases the exhalation plate 126 upward.

As shown in FIG. 17, during inhalation the inhalation flap 120 opens due to the negative pressure resulting from the inhalation which allows the patient to inhale the oxygen mixed with the ambient air. As shown in FIG. 18, during exhalation the inhalation flap 120 closes and exhalation plate 126 is pushed downward due to the positive pressure generated by the exhalation. As the exhalation plate 126 is pushed downward below the exhalation openings 124, the exhaled air exits the cannula 114 through the exhalation openings 124. Once exhalation ends, the PEP spring 122 will bias the exhalation plate 126 upwards again to cover the exhalation ports 124.

As the patients breathing cycles through inhalation and exhalation, the inhalation flap 120 will rise to allow the oxygen and air to be inhaled by the patient during inhalation, then as the patient exhales, the inhalation flap 120 closes, and the exhalation plate 126 lowers to expose the exhalation openings 124 to allow the exhaled air to exit the cannula. Next, as the patient takes their next breath, the exhalation plate 126 will rise back up blocking the exhalation openings 124 and the inhalation flap 120 will rise allowing the oxygen and air mixture to pass through to the patient.

The PEP spring is selected to provide the desired PEP value. The PEP spring 122 provides a static PEP value. The spring may be any of a variety of different types including for example a coil spring, a disk spring, an elastomeric spring, etc. A coil spring may provide varying PEP values by tightening the spring. Otherwise the PEP value may be varied by raising or lowering the spring in the cannula so that a different amount of force and hence pressure is required to move the spring past the exhalation opening. Further, the springs may be exchanged by the patient to provide different PEP values or even a plurality of different cannulas may be provided with different PEP values that then can be selected by the patient.

Figure 19:
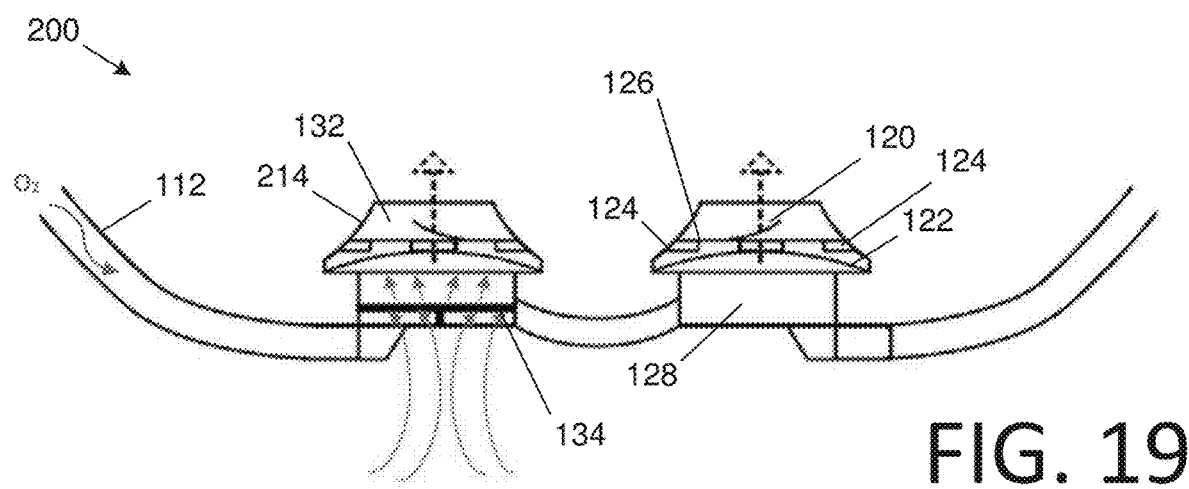
FIG. 19 illustrates another embodiment of the cannula.

FIG. 19 illustrates another embodiment of the cannula device 200 and cannula 214. Instead of using a venturi valve to draw in ambient air, this cannula 214 includes an ambient air valve 134 that allow ambient air to be drawn into to cannula body 128. In this case, the ambient air and the oxygen from the oxygen hose 112 mix in the cannula 214. Otherwise, the cannula 214 has the same structure as the cannula 114 and operates in the same manner.

The cannulas 114 and 214 may operate in a PEP only mode as previously described by using a plug to block any oxygen or ambient air flowing into the cannula.

Further, while the exhalation openings 124, inhalation flap 120, exhalation plate, and PEP string 122 are shown as part of the nasal interface, they may also be part of the body instead.

The PEP cannula device provides the ability to provide a patient oxygen therapy and PEP therapy in a single device that is compact, portable, and easy to use. The PEP cannula device may be used, for example, by oxygen-dependent COPD patients to aid and improve exercise tolerance and improve ability to maintain normal activities of daily living. The PEP cannula device may also be used in low, high, and pulse oxygen flow situations. The PEP cannula device also provides a static PEP value that can be chosen by the patient by swapping out parts or cannulas. The PEP cannula device may also be used in a PEP only mode as described without the oxygen therapy.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A cannula configured to provide positive expiratory pressure (PEP) and oxygen to a patient, comprising:
   a base including an oxygen opening and an inhalation opening;
   a valve including an inhalation flap that closes the inhalation opening and a PEP flap;
   a valve retainer including a flow opening and an exhalation opening, wherein the PEP flap closes the exhalation opening; and
   a nasal pillow seated on the valve retainer.

2. The cannula of claim 1, further comprising a nozzle including a plurality of nozzle openings in the oxygen opening of the base.

3. The cannula of claim 2, wherein the nozzle is configured to produce a venturi effect.

4. The cannula of claim 1, wherein the valve retainer further includes a flow opening wall, wherein an edge of the flow opening wall is an inhalation flap stop.

5. The cannula of claim 1, wherein
   the valve retainer includes a leg with a leg notch at an end of the leg, and
   the base includes a tab configured to engage the leg notch.

6. The cannula of claim 1, wherein the PEP flap is configured to provides a static PEP value.

7. The cannula of claim 1, wherein PEP flap includes a biasing member configured to provide a static PEP value.

8. The cannula of claim 1, further comprising a plug configured to be placed in the oxygen opening.

9. The cannula of claim 1, wherein the valve retainer includes an outer wall and wherein a portion of the outer wall adjacent to the exhalation opening is a PEP flap seal.

10. The cannula of claim 1, wherein the base further includes an oxygen opening wall, wherein an edge of the oxygen opening wall is an inhalation flap seal.

11. The cannula of claim 1, wherein the inhalation flap is configured to open the inhalation opening when the patient inhales.

12. The cannula of claim 1, wherein the PEP flap is configured to open the exhalation opening when the patient exhales and to provide a static PEP value.

13. A cannula device configured to provide positive expiratory pressure (PEP) and oxygen to a patient, comprising:
two cannulas wherein the cannulas each comprise:
a base including an oxygen opening and an inhalation opening;
a first valve including an inhalation flap that closes the inhalation opening and a PEP flap;
a valve retainer including a flow opening and an exhalation opening, wherein the PEP flap closes the exhalation opening; and
a nasal pillow seated on the valve retainer;
a connector connecting the two cannulas to one another; and
an oxygen hose configured to connect to each base.

14. The cannula device of claim 13, each of the cannulas further comprising a second valve, wherein the first and second valves have different PEP values and wherein the cannulas are configured to exchange the first and second valves.

15. The cannula device of claim 13, further comprising two plugs configured to be placed in the oxygen openings of the two cannulas.

16. The cannula device of claim 13, wherein each inhalation flap is configured to open the inhalation opening when the patient inhales.

17. The cannula device of claim 13, wherein each PEP flap is configured to open the exhalation opening when the patient exhales and to provide a static PEP value.

18. The cannula device of claim 13, wherein the two cannulas each further comprise a nozzle including a plurality of nozzle openings in the oxygen opening of each base.

19. The cannula device of claim 18, wherein each nozzle is configured to produce a venturi effect.

* * * * *